United States Patent [19]

Daniel et al.

[11] 4,277,492

[45] Jul. 7, 1981

[54] NOVEL 4-BIS((PHENYLMETHYL)AMINO)-BENZENESULFONIC ACIDS POSSESSING ANTIVIRAL ACTIVITY

[75] Inventors: John K. Daniel; Norton P. Peet, both of Indianapolis, Ind.

[73] Assignee: The Dow Chemical Company, Midland, Mich.

[21] Appl. No.: 152,000

[22] Filed: May 21, 1980

[51] Int. Cl.$^3$ ................ C07C 143/58; A61K 31/185; C07C 121/00; A61K 31/275
[52] U.S. Cl. ............................. 424/304; 260/465 E; 260/508; 260/509; 260/510; 424/315
[58] Field of Search ........... 260/508, 509, 510, 465 E; 424/304, 315

[56] References Cited

U.S. PATENT DOCUMENTS

| 622,854 | 4/1899 | Homolka et al. | 260/508 |
| 640,563 | 1/1900 | Homolka et al. | 260/508 |
| 648,261 | 4/1900 | Homolka et al. | 260/508 |
| 726,688 | 4/1903 | Homolka et al. | 260/508 |

OTHER PUBLICATIONS

Badische, Chem. Abstract, 55, 26460e (1960) (Abstract of German Patent 1,076,079).
Borecky, J. Chromatography, 9, 472 (1962).
Borodkin, J. Appl. Chem., USSR, pp. 741–743 (1955).

*Primary Examiner*—Nicky Chan

[57] ABSTRACT

Novel 4-bis((phenylmethyl)amino)benzenesulfonic acids and their pharmaceutically-acceptable salts are described. The compounds exhibit antiviral activity. Methods of using the compounds as antiviral agents are disclosed and also pharmaceutically-acceptable compositions.

15 Claims, No Drawings

NOVEL 4-BIS((PHENYLMETHYL)AMINO)-BENZENESULFONIC ACIDS POSSESSING ANTIVIRAL ACTIVITY

SUMMARY OF THE INVENTION

The present invention is directed to a compound of the formula:

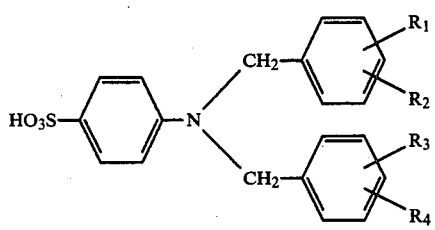

I wherein $R_1$ represents lower alkyl, lower alkoxy, nitro, amino, cyano, trifluoromethyl, acetyl, methylthio, methylsulfinyl, methylsulfonyl, aminosulfonyl or halogen; and $R_2$, $R_3$ and $R_4$ each independently represent hydrogen, lower alkyl, lower alkoxy, nitro, amino, cyano, trifluoromethyl, acetyl, methylthio, methylsulfinyl, methylsulfonyl, aminosulfonyl or halogen. The invention also includes the pharmaceutically-acceptable salts of the compounds described herein. Preferred compounds are those subject compounds in which $R_1$ represents halogen; and $R_2$, $R_3$ and $R_4$ each independently represent hydrogen or halogen.

As used herein, the term "halogen" represents bromo, chloro or fluoro; "lower alkyl" represents an alkyl group having from 1 to 3 carbon atoms, such as methyl, ethyl, propyl or isopropyl; "lower alkoxy" represents an alkoxy group having from 1 to 3 carbon atoms, such as methoxy, ethoxy, propoxy or isopropoxy; and "pharmaceutically-acceptable salts" refer to the acid addition salts of those bases which will form a salt with the benzenesulfonic acid and which will not cause an adverse physiological effect when administered to an animal at dosages consistent with good pharmacological activity. Suitable bases thus include, for example, the alkali metal and alkaline earth metal hydroxides, carbonates and bicarbonates, such as sodium hydroxide, potassium hydroxide, calcium hydroxide, potassium carbonate, sodium bicarbonate and magnesium carbonate.

In general, the compounds within the scope of the invention are solids having some water solubility which are also soluble to varying degrees in organic solvents such as methylene chloride, methanol and ethanol. The compounds disclosed herein exhibit antiviral activity and thus can be used to inhibit viral replication by contacting a virus and, preferably, virus host cells with an effective amount of the appropriate subject compound. The present invention is further directed to methods of using the compounds of the invention as antiviral agents in which a virus or virus host cell (i.e., a cell susceptible to infection by the virus) is contacted with an effective amount of one or more of the subject compounds. The present invention is also directed to antiviral compositions which can contain from about 0.00001 percent (%) or less to about 99% by weight of the active compoumd in combination with a pharmaceutically-acceptable carrier. Typically, in those compositions employing a low percentage of active compound, the pharmaceutically-acceptable carrier is in liquid form, therefore a composition containing 0.00001% or less by weight of active compound is equivalent to a composition containing about 0.1 microgram (μg) or less of the active compound per milliliter (ml) of carrier.

DETAILED DESCRIPTION OF THE INVENTION

Compounds within the scope of the present invention in which $R_1$ and $R_3$ are the same and $R_2$ and $R_4$ are the same are prepared by reacting a compound represented by Formula II, hereinafter referred to as sulfanilic acid:

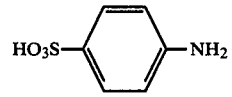

II with a ring-substituted benzyl halide of the general Formula III:

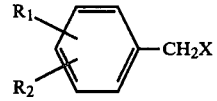

III wherein X represents bromide or chloride; and $R_1$ and $R_2$ have the same meanings as previously defined herein.

Reaction occurs when the ring-substituted benzyl halide, generally at a molar concentration slightly in excess of two times the sulfanilic acid molar concentration, is mixed with the sulfanilic acid in water in the presence of an alkaline agent, generally an alkali-metal hydroxide, such as sodium hydroxide or potassium hydroxide.

The reaction mixture is heated to a temperature of from about 70° C. to about 90° C. for approximately 18 to 22 hours; these conditions usually are sufficient to obtain the desired salt; however, longer or shorter reaction times and different reaction temperatures may, in some instances, be necessary or desirable. As the reaction proceeds, periodic additions of the alkaline agent may be required to maintain the reaction mixture at the desired pH, preferably about pH 11.

The free acid is obtained by treating the salt with an appropriate acid, such as hydrochloric acid. The salt or free acid is recovered from the reaction mixture by conventional procedures, for example, filtration, centrifugation or decantation. Purification of the product is accomplished by procedures well known in the art, such as recrystallization.

To prepare subject compounds in which either or both substituent $R_3$ or $R_4$ are different from the $R_1$ and $R_2$ substituents, a 4-((phenylmethyl)amino)benzenesulfonic acid or salt thereof containing the desired $R_1$ and $R_2$ substituents is reacted with approximately an equimolar amount of a ring-substituted benzyl halide in which the ring substituents are those selected for $R_3$ and $R_4$. Or a 4-((phenylmethyl)amino)benzenesulfonic acid or salt thereof containing the selected $R_3$ and $R_4$ substituents is reacted with approximately an equimolar amount of a ring-substituted benzyl halide in which the ring substituents are those selected for $R_1$ and $R_2$. The above reactions are conveniently accomplished employing reaction conditions substantially the same as those previously described herein. These compounds are also recovered and purified utilizing conventional methodology.

The 4-((phenylmethyl)amino)benzenesulfonic acids or salts thereof mentioned previously herein are prepared utilizing essentially the same procedures employed in making the 4-bis((phenylmethyl)amino)benzenesulfonic acids or salts thereof except that approximately equimolar concentrations of the ring-substituted benzyl halide and sulfanilic acid are used and, in general, shorter reaction times over a temperature range from about 40° C. to about 90° C. are employed.

Alternatively, the 4-((phenylmethyl)amino)-benzenesulfonic acid or salt thereof can be prepared by adding the appropriate ring-substituted benzyl halide (usually, as a solution of the benzyl halide in acetonitrile) to a mixture of sulfanilic acid in water and acetonitrile in the presence of a base such as sodium acetate or sodium acetate trihydrate. The resulting mixture is refluxed for a time sufficient to obtain the 4-((phenylmethyl)amino)-benzenesulfonic acid salt; usually a reflux time of about 2 to about 7 hours is sufficient. The free acid is obtained by treating the salt with an appropriate acid, such as hydrochloric acid. The salt or free acid can be recovered and purified by conventional procedures.

The following examples illustrate the invention, but are not to be construed as a limitation thereon.

EXAMPLE 1

4-(Bis((3-nitrophenyl)methyl)amino)benzenesulfonic Acid

A mixture of 25.75 grams (g) (0.15 mole) of sulfanilic acid in 450 milliliters (ml) of water, 37 g (0.46 mole) of 50 percent sodium hydroxide and 58.3 g (0.34 mole) of 3-nitrobenzyl chloride was stirred and heated to about 90° C. for 3½ hours, during which time the reaction mixture turned from a milky yellow to a reddish brown color. The solution was allowed to cool overnight and the resulting solid isolated by vacuum filtration. The solid was washed thoroughly with diethyl ether to remove excess 3-nitrobenzyl chloride, leaving 20.0 g of sodium 4-(bis((3-nitrophenyl)methyl)-amino)benzenesulfonate as shiny, yellow flakes having a melting point greater than 275° C. A 14.7 g portion of the sodium 4-(bis((3-nitrophenyl)methyl)amino)-benzenesulfonate was heated to 65° C. in approximately 350 ml of absolute ethanol and then acidified with concentrated hydrochloric acid. Upon cooling to room temperature, a solid crystallized which was recovered by vacuum filtration to give 10.0 g of 4-(bis((3-nitrophenyl)methyl)amino)benzenesulfonic acid as light tan crystals which decomposed at 226°–228° C.

Elemental analysis found carbon 53.92 percent, hydrogen 3.85 percent and nitrogen 9.55 percent, as compared to calculated values of carbon 54.17 percent, hydrogen 3.86 percent and nitrogen 9.48 percent.

EXAMPLE 2

4-(Bis((2,6-dichlorophenyl)methyl)amino)benzenesulfonic Acid

To a mixture of 18.7 g (0.109 mole) of sulfanilic acid in 175 ml of water was added a solution of 4.60 g (0.110 mole) of sodium hydroxide in 50 ml of water. To this dark solution was added 48.4 g (0.247 mole) of 2,6-dichlorobenzyl chloride, and the reaction solution was stirred at about 80° C. for 20 hours with periodic additions of 50 percent sodium hydroxide solution to keep the reaction solution at pH 11. The dark solution was cooled and the precipitate was collected, which yielded 19.1 g of solid. Washing with diethyl ether and air-drying afforded 16.4 g of the sodium salt. A second crop was collected, washed with diethyl ether and air-dried to give an additional 6.80 g of material. Total yield of the sodium salt was 23.2 g, (41.5 percent).

A 10.2 g portion of the sodium salt was slurried with 700 ml of water at 70° C. and acidified with concentrated hydrochloric acid. The gelatinous material was collected and oven-dried to yield 4.58 g of white solid. A 1 g portion of this solid was washed with water and oven-dried to yield 0.47 g of 4-(bis-((2,6-dichlorophenyl)methyl)amino)benzenesulfonic acid having a melting point greater than 240° C. Elemental analysis showed carbon 48.54 percent, hydrogen 2.92 percent and nitrogen 2.70 percent, as compared to calculated values of carbon 48.90 percent, hydrogen 3.08 percent and nitrogen 2.85 percent.

EXAMPLE 3

4-(Bis((4-fluorophenyl)methyl)amino)benzenesulfonic Acid

A mixture of 25.75 g of sulfanilic acid (0.15 mole) in 200 ml of water, 37 g (0.46 mole) of 50 percent sodium hydroxide solution and 50 g (0.344 mole) of 4-fluorobenzyl chloride was heated at approximately 80° C. for 18 hours. The reaction mixture was allowed to cool and then filtered to obtain a gray gelatinous material. The gelatinous material was washed with diethyl ether and then dissolved in hot absolute ethanol. The ethanol solution was acidified with concentrated hydrochloric acid resulting in the precipitation of a gray amorphous solid. A portion of the amorphous solid was washed with warm water to give 3.55 g of the product, 4-(bis((4-fluorophenyl)-methyl)amino)benzenesulfonic acid as an off-white powder having a melting point greater than 275° C.

An infrared spectrum (potassium bromide pellet) showed broad stretching from 3700–2300 cm$^{-1}$, and intense signals at 1620, 1590, 1495, 1460, 1430, 1240, 1120, 1110, 1035, 1015 and 910 cm$^{-1}$. A nuclear magnetic resonance spectrum (dimethylsulfoxide-d$_6$ solution) was as follows: δ7.77 (S, 1H, SO$_3$H), 7.57–6.60 (m, 12H, aromatic), 4.78 (S, 4H, both CH$_2$ groups).

EXAMPLE 4

4-(((4-Chlorophenyl)methyl)((4-fluorophenyl)-methyl)amino)benzenesulfonic Acid

A mixture of 16.0 g (0.053 mole) of sodium 4-(((4-fluorophenyl)methyl)amino)benzenesulfonate in 200 ml of water, 4.5 g (0.053 mole) of 50 percent sodium hydroxide and 9.75 g (0.06 mole) of 4-chlorobenzyl chloride was stirred at about 85° C. for 20 hours. The reaction mixture was cooled and then treated with diethyl ether. The aqueous layer was heated and acidified with concentrated hydrochloric acid. A light tan powder precipitated. Recrystallization gave the product 4-(((4-chlorophenyl)methyl)((4-fluorophenyl)-methyl)amino)-benzenesulfonic acid having a melting point greater than 250° C.

Elemental analysis found carbon 58.96 percent, hydrogen 4.38 percent and nitrogen 3.37 percent, as compared to calculated values of carbon 59.18 percent, hydrogen 4.23 percent and nitrogen 3.45 percent.

Other compounds falling within the scope of the present invention were prepared in essentially the same manner as previously described herein. These compounds are as follows.

EXAMPLE 5

4-(Bis((4-chlorophenyl)methyl)amino)benzenesulfonic Acid, melting point greater than 275° C.

Elemental analysis found carbon 56.83 percent, hydrogen 4.18 percent and nitrogen 3.04 percent, as compared to calculated values of carbon 56.87 percent, hydrogen 4.06 percent and nitrogen 3.32 percent.

EXAMPLE 6

4-(Bis((3-chlorophenyl)methyl)amino)benzenesulfonic Acid, melting point greater than 240° C.

Elemental analysis found carbon 56.67 percent, hydrogen 4.07 percent and nitrogen 3.42 percent, as compared to calculated values of carbon 56.87 percent, hydrogen 4.06 percent and nitrogen 3.32 percent.

EXAMPLE 7

4-(Bis((4-bromophenyl)methyl)amino)benzenesulfonic Acid, melting point greater than 270° C.

Elemental analysis found carbon 46.69 percent, hydrogen 3.43 percent and nitrogen 2.70 percent, as compared to calculated values of carbon 46.98 percent, hydrogen 3.35 percent and nitrogen 2.74 percent.

EXAMPLE 8

4-(Bis((2-fluorophenyl)methyl)amino)benzenesulfonic Acid, melting point greater than 230° C.

Elemental analysis found carbon 60.96 percent, hydrogen 4.74 percent and nitrogen 3.37 percent, as compared to calculated values of carbon 61.68 percent, hydrogen 4.40 percent and nitrogen 3.60 percent.

EXAMPLE 9

4-(Bis((3-fluorophenyl)methyl)amino)benzenesulfonic Acid, melting point greater than 240° C.

Elemental analysis found carbon 61.71 percent, hydrogen 4.24 percent and nitrogen 3.47 percent, as compared to calculated values of carbon 61.68 percent, hydrogen 4.40 percent and nitrogen 3.60 percent.

Antiviral activity for the subject compounds was demonstrated utilizing the following tissue culture testing procedure:

Monolayered HeLa cells in 16 millimeter (mm) tissue culture dishes were treated with 1 ml of culture medium (Eagles medium supplemented with fetal calf serum) containing compound at 100, 50, 25, 12.5, 6.25 or 0 µg/ml. Culture mediums such as those described herein are more fully described in standard tests, as for example, Kuchler's Biochemical Methods in Cell Culture and Virology, Dowden, Hutchinson and Ross, Inc., Stroudsberg, PA (1977). Immediately following treatment, cells were challenged with 0.05 ml of rhinovirus type 1A (RV-1A), rhinovirus type 2 (RV-2) or coxsackie $A_{21}$ virus (Cox $A_{21}$) in culture medium. Cell controls received no virus. Cultures were observed for compound cytotoxicity and viral cytopathic effect (CPE) at 48 and 72 hours post-treatment.

The subject compounds were also tested in animals as follows:

Swiss male mice, 10–12 g in weight, were challenged intraperitoneally (IP) with 0.2 ml of a normally lethal dose, i.e., a virus dose sufficient to cause ≈80–100 percent mortality in infected animals within 10 days of challenge, of Cox $A_{21}$ virus in phosphate buffered saline containing 1 percent heat inactivated fetal calf serum. Three hours later, mice were treated orally (PO) with 0.2 ml of compound suspended in 0.5 percent hydroxypropyl methylcellulose (Methocel) or with 0.2 ml of Methocel alone. The test compounds were administered at a 30 milligram/milliliter (mg/ml) concentration, which is a 600 milligram/kilogram (mg/kg) dosage. Mice were counted daily for 7–10 days post-challenge and deaths recorded. A modified Mantel-Haenzel combined chi-square ($X^2$) procedure was used to determine significant difference between virus control and treated groups. Chi-square values greater than 3.84 are considered significant (95 percent confidence level) in this test. Test results are shown in Table I.

TABLE I

| Compound Example No. | Cytotoxicity* (µg/ml) | Tissue Culture Testing** | | | Animal Testing | |
|---|---|---|---|---|---|---|
| | | RV-1A | RV-2 | Cox $A_{21}$ | Dose(PO) mg/kg | $\chi^2$ |
| 1 | 25.0 | 6.25 | NA | <6.25 | 600 | 0.117 |
| 2 | 12.5 | 6.25 | 12.5 | <6.25 | 600 | 0.731 |
| 3 | 100.0 | 12.5 | NA | <6.25 | 600 | 29.951 |
| 4 | 50.0 | 50.0 | NA | <6.25 | 600 | 39.4 |
| 5 | 25.0 | 12.5 | NA | <6.25 | 600 | 44.6 |
| 6 | 100.0 | >50.0 | NA | <6.25 | 600 | 27.4 |
| 7 | 25.0 | 12.5 | NA | <6.25 | 600 | 20.78 |
| 8 | 100.0 | NA | NA | <6.25 | 600 | 0.148 |
| 9 | 100.0 | 50 | NA | 12.5 | 600 | 6.408 |

*Cytotoxicity figures represent the concentration of compound (µg/ml) found to be toxic to the cell.
**Lowest concentration of compound (µg/ml) necessary to cause a 50 percent reduction in cytopathic effect.
The symbol "NA" indicates that the test compound was not active against that particular test virus at the standard test conditions; ">" means "greater than"; "<" means "less than".

The data in Table I demonstrate the antiviral activity of representative compounds falling within the scope of the present invention.

The tissue culture test data indicate that all the tested compounds are active against at least one of the three test viruses, (RV-1A, RV-2 or Cox $A_{21}$). In addition, compound Example Nos. 3, 4, 5, 6, 7 and 9 (at the 95 percent confidence level) show that they are active antiviral compounds in testing with mice.

In using the compounds of the invention, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner which ensures continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating picornaviruses. Contacting can also be carried out by administering an antiviral dosage of a compound of the invention to an animal (preferably a mammal). The compounds can be administered to animals parenterally (for example, by intraperitoneal, subcutaneous or intravenous injection) or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds when administered to tissue culture medium exhibit significant antiviral activity at low concentrations, as for example, the finding that a concentration of 6.25 μg/ml or less of a subject compound was often sufficient to cause a 50% reduction in cytopathic effect against a particular test virus in the tissue culture testing.

Such compositions can contain from about 0.1 microgram or less of the active compound per milliliter of carrier to about 99 percent by weight of the active compound in combination with a pharmaceutically-acceptable carrier.

Preferred compositions include compositions containing from about 0.1 μg to about 5 μg of active compound per milliliter of carrier to about 0.0025 to about 0.05 to about 0.25 to about 0.5 to about 1 to about 10 to about 25 to about 50 percent by weight of active compound in a pharmaceutically-acceptable carrier.

The compositions can be in solid forms such as tablets, capsules, granulations, feed mixes, feed supplements and concentrates, powders, granules or the like; as well as liquid forms such as sterile injectable suspensions, orally administered suspensions, or solutions. The pharmaceutically-acceptable carriers can include excipients such as surface active dispersing agents, suspending agents, tableting binders, lubricants, flavors and colorants. Suitable excipients are disclosed, for example, in texts such as Remington's Pharmaceutical Manufacturing, Thirteenth Edition, Mack Publishing Co., Easton, PA. (1965).

What is claimed is:

1. A compound of the formula:

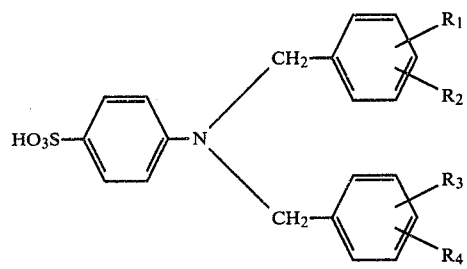

and the pharmaceutically-acceptable salts thereof wherein $R_1$ represents lower alkyl, lower alkoxy, nitro, amino, cyano, trifluoromethyl, acetyl, methylthio, methylsulfinyl, methylsulfonyl, aminosulfonyl or halogen; and $R_2$, $R_3$ and $R_4$ each independently represent hydrogen, lower alkyl, lower alkoxy, nitro, amino, cyano, trifluoromethyl, acetyl, methylthio, methylsulfinyl, methylsulfonyl, aminosulfonyl or halogen.

2. The compound of claim 1 wherein $R_1$ represents halogen; and $R_2$, $R_3$ and $R_4$ each independently represent hydrogen or halogen.

3. The compound of claim 1 which is 4-(bis((3-nitrophenyl)methyl)amino)benzenesulfonic acid or a pharmaceutically-acceptable salt thereof.

4. The compound of claim 1 which is 4-(bis((2,6-dichlorophenyl)methyl)amino)benzenesulfonic acid or a pharmaceutically-acceptable salt thereof.

5. The compound of claim 1 which is 4-(bis((4-fluorophenyl)methyl)amino)benzenesulfonic acid or a pharmaceutically-acceptable salt thereof.

6. The compound of claim 1 which is 4-(((4-chlorophenyl)methyl)((4-fluorophenyl)methyl)-amino)benzenesulfonic acid or a pharmaceutically-acceptable salt thereof.

7. The compound of claim 1 which is 4-(bis((4-chlorophenyl)methyl)amino)benzenesulfonic acid or a pharmaceutically-acceptable salt thereof.

8. The compound of claim 1 which is 4-(bis((3-chlorophenyl)methyl)amino)benzenesulfonic acid or a pharmaceutically-acceptable salt thereof.

9. The compound of claim 1 which is 4-(bis((4-bromophenyl)methyl)amino)benzenesulfonic acid or a pharmaceutically-acceptable salt thereof.

10. The compound of claim 1 which is 4-(bis((2-fluorophenyl)methyl)amino)benzenesulfonic acid or a pharmaceutically-acceptable salt thereof.

11. The compound of claim 1 which is 4-(bis((3-fluorophenyl)methyl)amino)benzenesulfonic acid or a pharmaceutically-acceptable salt thereof.

12. A method for inhibiting viruses which comprises contacting viruses or virus host cells with an effective virus inhibiting amount of a compound corresponding to the formula:

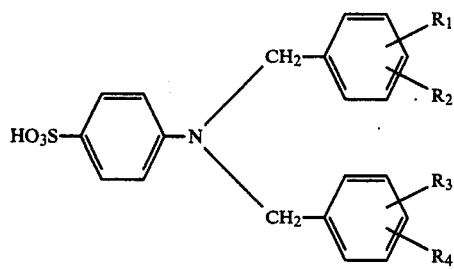

and the pharmaceutically-acceptable salts thereof wherein $R_1$ represents lower alkyl, lower alkoxy, nitro, amino, cyano, trifluoromethyl, acetyl, methylthio, methylsulfinyl, methylsulfonyl, aminosulfonyl or halogen; and $R_2$, $R_3$ and $R_4$ each independently represent hydrogen, lower alkyl, lower alkoxy, nitro, amino, cyano, trifluoromethyl, acetyl, methylthio, methylsulfinyl, methylsulfonyl, aminosulfonyl or halogen.

13. The method of claim 12 wherein $R_1$ represents halogen; and $R_2$, $R_3$ and $R_4$ each independently represent hydrogen or halogen.

14. A virus inhibiting composition comprising a pharmaceutically-acceptable carrier and an effective virus inhibiting amount of a compound corresponding to the formula:

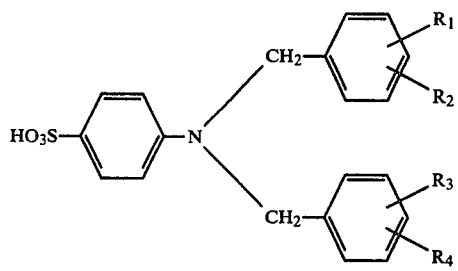

and the pharmaceutically-acceptable salts thereof wherein $R_1$ represents lower alkyl, lower alkoxy, nitro, amino, cyano, trifluoromethyl, acetyl, methylthio, methylsulfinyl, methylsulfonyl, aminosulfonyl or halogen; and $R_2$, $R_3$ and $R_4$ each independently represent hydrogen, lower alkyl, lower alkoxy, nitro, amino, cyano, trifluoromethyl, acetyl, methylthio, methylsulfinyl, methylsulfonyl, aminosulfonyl or halogen.

15. The composition of claim 14 wherein $R_1$ represents halogen; and $R_2$, $R_3$ and $R_4$ each independently represent hydrogen or halogen.

* * * * *